US008568774B2

(12) United States Patent
Lynch et al.

(10) Patent No.: US 8,568,774 B2
(45) Date of Patent: Oct. 29, 2013

(54) HOMOGENEOUS GAS-EVOLVING COMPOSITION

(75) Inventors: James R. Lynch, Toledo, OH (US); Timothy D. Birthisel, Perrysburg, OH (US); Jeffrey J. Fesko, Maumee, OH (US)

(73) Assignee: The Andersons, Inc., Maumee, OH (US)

( * ) Notice: Subject to any disclaimer, the term of this patent is extended or adjusted under 35 U.S.C. 154(b) by 699 days.

(21) Appl. No.: 12/701,775

(22) Filed: Feb. 8, 2010

(65) Prior Publication Data

US 2010/0248966 A1 Sep. 30, 2010

Related U.S. Application Data

(63) Continuation-in-part of application No. 11/327,098, filed on Jan. 6, 2006, now Pat. No. 7,658,948.

(60) Provisional application No. 60/642,318, filed on Jan. 7, 2005.

(51) Int. Cl.

| | |
|---|---|
| ***A61K 9/54*** | (2006.01) |
| ***A61K 9/14*** | (2006.01) |
| ***A01N 57/00*** | (2006.01) |
| ***A01N 57/18*** | (2006.01) |
| ***A01N 43/72*** | (2006.01) |
| ***A01N 43/40*** | (2006.01) |
| ***A01N 43/36*** | (2006.01) |

(52) U.S. Cl.
USPC ........... 424/458; 424/489; 504/127; 504/201; 504/206; 504/222; 504/244; 504/254; 504/260; 504/284; 504/285; 504/307

(58) Field of Classification Search
None
See application file for complete search history.

(56) References Cited

U.S. PATENT DOCUMENTS

| | | | | |
|---|---|---|---|---|
| 5,948,439 | A | 9/1999 | Forman et al. | |
| 6,200,928 | B1 * | 3/2001 | Kawai | 504/117 |
| 6,506,713 | B1 | 1/2003 | Slavtcheff et al. | |
| 6,800,597 | B2 | 10/2004 | Campagnoli | |

FOREIGN PATENT DOCUMENTS

| | | | |
|---|---|---|---|
| JP | 07112904 | * | 5/1995 |
| JP | 07112904 | A | 5/1995 |

* cited by examiner

*Primary Examiner* — Alton Pryor

(74) *Attorney, Agent, or Firm* — Blue Filament Law PLLC; Avery N. Goldstein

(57) ABSTRACT

A homogeneous gas-evolving composition is provided that includes an acid, a gas-evolving acid neutralizing agent, and at least one of an inorganic carbonate, inorganic bicarbonate, alkaline peroxide, or alkaline azide. A water-soluble desiccant is homogeneously intermixed with the acid and the gas-evolving acid neutralizing agent. The desiccant is present in an amount able to absorb ambient moisture equivalent to at least 0.01 total weight percent of the composition before gas evolution of more than 50% of the theoretical gas evolution available from the composition. To confer storage stability, the acid, the gas-evolving acid neutralizing agent, and water-soluble desiccant cumulatively have a water content of less than 1 total weight percent water. Through appropriate selection of a desiccant or inclusion of a surfactant foaming agent, the composition foams upon drenching with water. The composition is particularly well suited for consistent usage of glyphosate herbicide. Plant growth inhibition is provided by wetting a plant with water and then applying the composition onto the plant. After allowing sufficient time, the composition absorbs the water and evolves gas, thereby spreading herbicide on the plant preferential to surrounding soil.

12 Claims, No Drawings

HOMOGENEOUS GAS-EVOLVING COMPOSITION

CROSS-REFERENCE TO RELATED APPLICATIONS

This application is a continuation-in-part of U.S. patent application Ser. No. 11/327,098 filed Jan. 6, 2006, now U.S. Pat. No. 7,658,948, which claims priority of U.S. Provisional Patent Application Ser. No. 60/642,318 filed Jan. 7, 2005, which is incorporated herein by reference.

FIELD OF THE INVENTION

The present invention in general relates to a pelletized composition in the form of a dispersible granule, pellet, stick or powder for use in plant culture or for de-icing and anti-icing of paved surfaces and equipment and, in particular, to a pelletized composition with storage stability that foams upon contact with water.

BACKGROUND OF THE INVENTION

In the course of a growing season, modern plant culture dictates multiple treatments with fertilizer and pesticide; and in winter, where snow and ice are present for periods of time, proper property and equipment (e.g. aviation) maintenance requires the application of de-icing and anti-icing materials. A practitioner of plant culture must decide whether a particular treatment is best performed with a granular product or a liquid spray application. Crops as diverse as turf, grain crops, tubers, ground fruits and vegetables, and horticultural plantings are routinely treated with either granular or sprayed substances. Facility and equipment maintenance operations likewise employ either granular de-icers or liquid compositions, so a similar choice must be made by that practitioner. Each application method has limitations. Specifically, while granule broadcast tends to provide a simple broadcast, generally long-term release and safe handling, granules are difficult to adhere to plant and equipment surfaces, create concentration gradients about each granule, and represent an ongoing potential toxin or physical entity that can be inadvertently contacted or ingested by humans or fauna, or pose mechanical problems for equipment such as maintenance and aviation equipment. In contrast, spray treatment generally requires considerable skill for application, contacts only exposed foliage and equipment and surfaces receiving indirect drainage from other surfaces, and tends to dissipate, or "run off", quickly. Some sprays such as anti-icers to surfaces or fruit crops require the use of expensive polymers and additives in order to prolong the "holdover time", or length of time the equipment may be allowed to stand ice free. Based on these treatment characteristics, pesticides targeting weed leaves or foliage-feeding pests and de-icers and anti-icers targeting equipment surfaces tend to be applied as a liquid spray, while fertilizers and pesticides targeting weed seeds, grubs and other soil-dwelling pests and de-icers and anti-icers targeting paved surfaces often are delivered as granules. Regardless of whether spray or granule broadcast is used, the application method is not completely satisfactory. For instance, spray application fails to reach pests dwelling on the underside of foliage and is quickly dissipated and leached into soil by rain, and liquid de-icers and anti-icers can cause environmental wastewater management problems because a significant excess amount of product must be used in order to allow for adequate contact time.

Granular pesticide formulations often require the use of additional pesticide due to inefficiencies in the timely release, or efficient environmental extraction, of the pesticide from the associated granular substrate materials.

While there exists a need for a granule that, through foaming upon contact with water, has desirable attributes of both granule, broadcast and spray treatment for use in plant culture and/or in de-icing and anti-icing, the moisture reactivity of components needed to induce foaming has left prior art products vulnerable to ambient humidity premature activation. This has been addressed in the prior art of cosmetics through the inclusion of dried medicinal herbs in a sachet or granule, such as in products detailed in U.S. Pat. Nos. 5,948,439; 6,800,597; and 6,506,713. Unfortunately, the natural oils are degraded by drying to a low water content. Additionally, dried plant stuffs such as leaves, roots, or stalks of medicinal herbs suffer from low moisture absorption, low densities, and enhance pelletized composition porosity. Segregation of components into separate layers of a granule largely overcomes ambient humidity premature activation but at the expense of a more complicated process of manufacture. While a binder has previously been used to adhere particulate into a granule or other form, little attention has been paid to inclusion of a binder material or biomaterial that has been present in an amount and at a dryness level to enhance the storage stability of the resultant composition.

Thus, there exists a need for a gas-evolving homogeneous composition that is insensitive to ambient humidity premature gas evolution. There further exists a need for such a composition that lacks a surface coating to prevent ambient humidity premature gas evolution.

SUMMARY OF THE INVENTION

A homogeneous gas-evolving composition is provided that includes an acid, a gas-evolving acid neutralizing agent, and at least one of an inorganic carbonate, inorganic bicarbonate, alkaline peroxide, or alkaline azide. A water-soluble desiccant is homogeneously intermixed with the acid and the gas-evolving acid neutralizing agent. The desiccant is present in an amount able to absorb ambient moisture equivalent to at least 0.01 total weight percent of the composition before gas evolution of more than 50% of the theoretical gas evolution available from the composition. To confer storage stability, the acid, the gas-evolving acid neutralizing agent, and water-soluble desiccant cumulatively have a water content of less than 1 total weight percent water. Through appropriate selection of a desiccant or inclusion of a surfactant foaming agent, the composition foams upon drenching with water. The composition is particularly well suited for consistent usage of glyphosate herbicide. Plant growth inhibition is provided by wetting a plant with water and then applying the composition onto the plant. After allowing sufficient time, the composition absorbs the water and evolves gas, thereby spreading herbicide on the plant preferential to surrounding soil.

DETAILED DESCRIPTION OF THE PREFERRED EMBODIMENTS

The present invention has utility as a composition to deliver a substance beneficial to plant culture. An inventive granule, upon contact with water, releases gas to create a foam that spreads the granule contents beyond the dimensions of the granule. The use of an inventive granule achieves superior handling and active ingredient usage as compared to the conventional art. Through the inclusion of a desiccant in an amount and level of dryness, a storage stable, homogeneous foaming composition is compressed into various forms thereby simplifying manufacture relative to a core-shell segregation between a solid acid-neutralizing agent and an acid.

As used herein, "storage stable" in the context of an inventive composition is defined as a composition that evolves less than 5% of the theoretical gas-evolving capacity of the composition in a 24 hour period at 20° Celsius and a relative humidity (rh) expressed as a percentage measured in air compared to maximal storage capacity of 70% at 760 torr barometric pressure.

Additionally, the use of a foaming mechanism offers another tool for pest control, which may augment or replace the traditional pesticide material in certain cases. By generating a gas, along with a temporary containment for the gas, which may be directly toxic to, or which may alter the behavior of certain animal pests, the invention may serve as a pesticide or synergist in its own right. In a preferred embodiment a polypeptide, polysaccharide, or synthetic polymer serves as the desiccant to also afford a controlled viscosity gel upon water sealing to generate a foaming mass without resort to an ionic surfactant.

The foaming mechanism as applied to de-icers can significantly enhance product distribution, adhesion, penetration of ice/snow cover, and separation of ice/snow from the treated surfaces due to the chemical and kinetic energy it provides. Likewise, the mechanism may enhance the use of exothermic energy (from dissolution of certain salts, e.g. calcium chloride).

The present invention incorporates a solid acid-neutralizing agent and an acid that are not completely reactive until solvated with water. Neutralization of the acid component by a carbonate, peroxide, or azide liberates a gas that functions as a propellant to expand a foaming agent present within a composition according to the present invention. A gas-evolving neutralizing agent according to the present invention generates a gas such as carbon dioxide, nitrogen or oxygen upon reaction with the acid in the presence of water. A carbonate, peroxide, or azide operative in the present invention as a neutralizing agent is one capable of neutralizing acid. Carbonates operative herein include carbonates where the cation is an alkali metal, alkali earth, hydrogen, ammonium, tetraorganal ammonium, transition metals, alone, or in combination with hydrogen. Peroxides operative herein illustratively include sodium perforate and sodium percarbonate. Sodium azide is an exemplary azide operative herein. It is appreciated that in selecting a carbonate, peroxide, or azide, the tolerance of a target plant and the healthy soil ecosystem surrounding the plant towards the carbonate, peroxide, or azide are important considerations. It is further appreciated that formation of a localized carbon dioxide environment has insecticidal properties. Specific examples of carbonates operative herein illustratively include sodium carbonate, sodium bicarbonate, magnesium carbonate, calcium carbonate, aluminum carbonate, and ammonium carbonate. It is appreciated that inventive carbonate is typically in the form of a mineral particulate. Additionally, it is appreciated that the ability of a carbonate to neutralize acid, and in the process deliver a carbon dioxide, is largely independent of the nature of the cation and as such, the choice of a particular carbonate is dictated by factors illustratively including cost, ease of processing, and secondary soil conditioning properties. By way of example, a soil deficient in a particular element such as calcium or magnesium derives a secondary soil conditioning benefit from the use of these respective carbonates. Likewise, ammonium carbonate, after acid neutralization, provides a bioavailable nitrogen source. The gas-evolving neutralizing agent is present from 1 to 60 wt. %; preferably the gas-evolving neutralizing agent is present in a stoichiometric amount relative to the acid equivalents of the acid component.

A pre-dried biomaterial desiccant is provided to render an inventive composition stable relative to ambient humidity to extend storage stability duration and into high humidity climates and seasons. By reducing the desiccant inherent moisture content, the desiccant becomes a sink for absorption of ambient moisture that would otherwise initiate foaming reaction between the acid and acid-neutralizing agent. A desiccant operative herein is characterized by being water soluble to an amount of at least 0.01 molar for monomeric desiccants and 0.0001 molar of polymeric desiccants. According to the present invention, it has been found that desiccant hydration occurs at the expense of gas-evolving reaction between the pelletized acid and acid-neutralizing agent components thereby inhibiting gas evolution associated with storage exposure to ambient humidity and moisture.

Biomaterial molecular desiccants operative herein include the sugars glucose, mannose, fructose, galactose, sucrose, lactose, maltose, xylose, arabinose, trehalose and mixtures thereof such as corn syrup, maple syrup, or molasses, urea, and methylene urea. Biomaterial polymeric desiccants operative herein include lignin and lignin derivatives such as calcium lignosulfate, ammonium lignosulfonate, sodium lignosulfate, and nitrolignin; humus, humic acid, fulvic acid, and salts thereof including calcium, sodium, ammonium, and/or sulfonate salts; cellulose, hemicellulose, and cellulose derivatives such as carboxymethylcellulose, ethylcellulose, hydroxyethylcellulose, hydroxy-methylethylcellulose, hydroxyethylpropylcellulose, methylhydroxyethyl-cellulose, methylcellulose; starches such as amylose, seagel, starch acetates, starch hydroxyethyl ethers, ionic starches, long-chain alkyl starches, dextrins, amine starches, phosphate starches, and dialdehyde starches; plant starches such as rice starch, corn starch and potato starch; other carbohydrates such as pectin, amylopectin, xylan, glycogen, and alginic acid; proteins such as single cell organism protein, soy extract, zein, protamine, albumen, collagen, casein, alginate, and any type of plant, fungal, crustacean, planktonic, fish, or meat protein, or their derivatives. Biomaterial desiccants generally include any material which may be called "biomass". The biomaterial desiccant operative herein specifically excludes dried plant particulate of individual cells, leaves, stems, or roots and also excludes yeast extracts that appear to act as a microbial growth medium. It is appreciated that the biomaterial desiccants have previously been employed as binders to aggregate particulate into a granular form; the loadings of a particular desiccant are increased relative to the amount used as a binder to provide needed desiccation capacity. The present invention recognizes for the first time the unexpected ability of these binders to achieve storage stability as to pelletized material effervescence. Other desiccants which are operative herein include DRIERITE®, silica gel, calcium sulfate, calcium chloride, chalk, activated alumina, aluminum oxide, Aerogel, benzophenone, bentonite clay, boric anhydride, montmorillonite clay, calcium chloride, calcium hydride, calcium oxide, cobalt(II) chloride (also a color changing moisture indicator), copper(II) sulfate, lithium chloride, lithium hydride, lithium aluminum hydride, lithium bromide, magnesium, magnesium oxide, magnesium sulfate, magnesium perchlorate, molecular sieve, NaK, a sodium-potassium alloy, phosphorus pentoxide, potassium, potassium carbonate, potassium chloride, sodium, sodium chlorate, sodium chloride, sodium hydroxide, sodium sulfate, sodium-benzophenone, and zinc chloride.

While a binder is routinely solvated with water to form a desired viscosity syrup before addition to particulate component mixture that is then dried as for example in a pan agglomerator to form granules, such a process is inapplicable to an inventive composition as an aqueous component addition would cause acid neutralization that expends the gas evolution capability during manufacture. An inventive homogeneous composition is instead formed by mixing dried acid, acid neutralizer, desiccant, and other optional additive components in the presence of an aprotic polar solvent system containing less than 0.01% by weight of the total solvent being water. Preferably, the inventive composition components are dried to a cumulative moisture content of less than 1 total weight percent as measured by Karl Fischer titration, and more preferably to between 0.02 and 0.08 moisture as total weight percent, again as measured by Karl Fischer titration. The majority of the aprotic polar solvent is alcohols such as $C_1$-$C_{12}$ alkyl alcohols, $C_2$-$C_{24}$ alkyl esters, and heteroatom containing polar solvents such as formamide, dimethyl sulfoxide, and various polymers such as polyethylene glycol. Preferably, the aprotic polar solvent system is non-VOC as currently defined by U.S. EPA regulations. More preferably, upon removal of the aprotic polar solvent system used to intermix inventive composition components to a homogeneous form, the solvent is reclaimed, optionally purified, and reused to form additional inventive composition. A homogeneously mixed yet solvent system wetted inventive composition is then formed by conventional techniques into a variety of sizes and shapes of granules, pellets, or sticks. The inventive compositions so manufactured have superior storage stability due to the biomaterial desiccant interactions with trace amounts of water used in the formulation or that comes into contact during manufacturing or storage to inhibit premature reactions in the inventive composition that cause the effervescence potential to fall during product manufacture and/or storage. Additionally, the biomaterial desiccant does not materially interfere with the effervescence of the inventive composition during flooding (typically with water) and the time of product use, due to the limited holding capacity and relatively slow rate of bonding, and owing to the general compatibility with many use sites in natural and agronomic settings as well as uses in proximity with animals and people.

The presence of biomaterial desiccant facilitates the inclusion of other additives such as humectants or adhesives that can provide enhanced functionality such as dispersion, spreading, sticking, foam stabilization, gas trapping, attractancy, repellency, and resistance to loss from weathering, chemical- or light-induced degradation, among many other functions. The net result of the inclusion of biomaterials and related substances is practically robust formulations with a variety of functionalities and compositions that have reduced associated manufacturing and storage complexity and cost.

The only requirements as to the identity of an acid operative in the present invention are that the acid have a pKa value sufficient to generate a high enough proton ion concentration to induce active carbon dioxide generation and that the acid salt be compatible with plant culture, Preferably, the acid is in a solid and dry form. An important component of an inventive granule is the acidic material. Suitable for this purpose are any acids present in dry solid form. Acids operative herein include $C_2$-$C_{20}$ organic mono- and poly-carboxylic acids and especially alpha- and beta-hydroxycarboxylic acids; $C_2$-$C_{20}$ organophosphorus acids such as phytic acid; and $C_2$-$C_{20}$ organosulfur acids such as toluene sulfonic acid. Typical hydroxycarboxylic acids include gluconic, glucoheptonic, 2-hydroxyisovaleric, tartaric, lactic, salicylic and citric acids as well as acid-forming lactones such as gluconolactone and glucarolactone. Still other specific acids operative herein illustratively include formic, acetic, propionic, butyric, valeric, caproic, caprylic, capric, lauric, myristic, palmitic, stearic, oleic, linoleic, linolenic, propionic, benzoic, toluic, anthranilic, and acrylic, as well as dicarboxylic acids such as oxalic, adipic, glutaric, succinic, malonic, succinic, glutaric, adipic, maleic, fumaric, malic, maleic, and phthalic acids. Most preferred is citric acid. Also suitable as acid materials are solid acid forms of biologically active ingredients (BAIs) alone or in combination with other recited acids such that the effervescing reaction not only provides biologically active gas and physical spreading action and other features described herein, but also converts the BAI, often initially manufactured in the acid form, into a frequently preferred salt form of the BAI. The salt form is a more soluble version of the BAI that normally requires a separate manufacturing step, diluents, purification, and liquid packaging systems, as well as heated storage in order to prevent freezing, settling, crystallization and other problems prior to use. The BAI salts are often preferred since they may be more readily translocated over and into biological membranes and in vascular systems, are more readily distributed in wet areas, and are less prone to undesired chemical reactions which may negate the BAI activity. The invention therefore offers additional BAI functionality from BAI acids at reduced cost. Representative BAIs which are converted from the acid to salt forms through effervescence are the herbicides glyphosate, glufosinate, clopyralid, bentazon, picloram, triclopyr, phenoxy-, acetic-, phthalmic- and benzoic-acid derivatives; the insecticides boric acid, pelargonic, nonanoic; and fatty acids for use as insecticides, herbicides, fungicides, and algaecides; growth regulators gibberellic acid, GABA, atrimmec, trinexepac-ethyl, I-naphthalenacetic acid, phthalmic acid, 3-CPA, indolebutyric acid, 4-chlorphenoxyacetic acid, CHPA, deltrol, clofencoet, 1-lactic acid, and the fungicide phosphorus acid. Glyphosate, a conventional herbicide, is delivered to plant leaves with especially good effect through foaming as there is little effect of glyphosate upon contacting soil.

Because the effervescing reaction of this inventive composition typically produces salts that dissolve immediately, there is also opportunity to take advantage of the exothermic and endothermic properties of solution formation for practical benefit. Examples of these benefits include exothermic heating improving the function of de-icing products and/or frost/freeze preventers, and endothermic cooling assisting in reducing the ability of pests to escape the controlling influence of the BAI.

Optionally, an acid salt of the acid used is present as a pH buffer and to provide storage stability to the resulting composition.

A surfactant foaming agent is present to entrain carbon dioxide emitted upon neutralization reaction between the acid and the gas-evolving neutralizing agent. While it is preferred that a desiccant provide a foaming function, a surfactant foaming agent, if present, is typically present from 0.01 to 10 per weight percent. Surfactant foaming agents operative herein illustratively include sopinin; anionic surfactants, such as fatty acid esters, alkyl sulfates, alkylarylsulfonates, such as alkylbenzene sulfonates; alkyl sulfonates; isocyanates, such as methylenedisocyanate and tolylene diisocyanate, and non-ionic surfactants, such as polyoxyethylene alkyl phenols, polyoxyethylene fatty acids esters, polyoxyethylene alcohols, polyoxyethylene mercaptans, polyoxyethylene alkylamines, polyol esters, phosphate esters, alkyl mono- or polyglycosides, sorbitan esters, polymers of ethylene oxide, propylene oxide, and/or butylene oxide, vegetable oil glycerides, glycerol esters, silicones, and various compounds containing amide groups. Nonionic surfactants are preferred as being less hygroscopic relative to ionic surfactants.

An inventive granule includes an active ingredient such as a plant growth enhancer, a de-icer, an anti-icer, a pest control agent fertilizer, and a combination thereof. An active ingredient is typically present in an amount ranging from 0.05% to 50% by weight of the total dry weight of the particle. In a more preferred embodiment, the active ingredient is present in an amount ranging from 0.1% to 30% by weight of the total dry weight of the granule. In a still more preferred embodiment, the active ingredient is present in an amount ranging from 0.5% to 10% by weight of the total dry weight of the particle. Optionally, a foam stabilizing agent is included in order to maintain the presence of the foam over time. Compounds such as glycerin, hydrolyzed protein, synthetic polymers, or any of a number of long chain polar compounds with straight chain hydrocarbon groups of about the same length as the surfactant, may serve this purpose.

As used herein, a plant growth enhancer is defined as a substance that enhances the growing medium in which a plant resides. A plant growth enhancer specifically includes a bioavailable source of nitrogen, potassium, or phosphorus; a soil nutrient; a soil amendment material; and a biostimulant. Exemplary fertilizers and de-icers include urea, sulfur-coated urea, isobutylidene diurea, ammonium nitrate, ammonium sulfate, ammonium phosphate, triple super phosphate, phosphoric acid, potassium sulfate, potassium nitrate, potassium metaphosphate, potassium, dipotassium carbonate, potassium oxide and a combination thereof. It is appreciated that pH control must be exercised to prevent evolution of ammonia gas when combining a bioavailable nitrogen source into an inventive pelletized granule composition.

Exemplary soil nutrients include calcium, magnesium, sulfur, iron, manganese, copper, zinc; oxides thereof; salts thereof, and a combination thereof.

Exemplary amendment materials include humic acid, blood meal, bone meal, seed meal, feather meal, soy meal, meat meal, animal waste, activated sludge, hydrolyzed animal hair, a fish byproduct, chitin, composts and a combination thereof. In addition, a fertilizer particle optionally includes an additive to aid in particle formation illustratively including an anti-dust agent, an anti-caking agent, a filler, a preservative, and a combination thereof.

Biostimulants are substances that promote plant survival and health and illustratively include plant growth hormones and plant growth regulators such as cytokinins, auxins, gibberellins, ethylene, absisic acid and a combination of these. A biostimulant is optionally included as a secondary active ingredient in an amount ranging from 0.05% to 10% by weight of the total dry weight of the particle. In a more preferred embodiment, the biological factor or biostimulant active ingredient is present in an amount ranging from 0.1% to 5% by weight of the total dry weight of the particle. In a still more preferred embodiment, the biological factor or biostimulant active ingredient is present in an amount ranging from 0.25% to 1% by weight of the total dry weight of the particle.

Exemplary de-icers include glycols, salts of carboxylic acids, sodium chlorides, magnesium chlorides, and calcium chlorides. Exemplary anti-icers illustratively include thickened aqueous alcohols as detailed in U.S. Pat. No. 5,772,912 or a de-icer that affects the colligative properties of water to depress the freezing temperature below −10° C.

In another embodiment, an inventive granule includes as a BAI a pest control agent for killing or inhibiting infestation by a target pest organism includes an arachnid; a bacterium; a bird; a fungus; an insect; a mammal, such as a rodent; a mollusk, such as a snail or a slug; a virus; and a worm. The pest control agent is appreciated to be operative not only in being lethal to the pest but also by being repellant or lessening the reproductive fitness of the pest.

A BAI whether present in foamable acid form or as a salt includes agents such as an acaracide; an antimicrobial; a bactericide; an entomopathogen; a fungicide; a synthetic plant growth regulator such as a gibberlic acid synthesis inhibitor or promoter; an herbicide; an insecticide; a molluskicide; a nemacide; a rodenticide; a pheromone; a chemosterilant; a viricide; an imagocide; a larvicide; an ovicide; a formicide; an aphidicide; a muscacide; a culicicide; an anophelicide; an arachnidcide; and a vespacide. With the exception of a rodenticide, an inventive composition optionally contains a mammalian and/or avian ingestion repellant to lessen the likelihood of incidental ingestion by bystander higher species. Mammalian ingestion repellants illustratively include cadaverine, butyric acid, and capsaicin. Avian repellants include artificial grape flavorant.

A BAI functioning as a pest reproductive control agent operative herein includes a pheromone, molting signaling compound or steroid that upon contact with the target pest decreases the reproductive capacity of the pest. A pest reproductive control agent is preferred over a pesticide since a reproductive control agent is specific to a species or narrower group of organisms, does not bioaccumulate, and is less detrimental to predatory or bystander organisms in the pest habitat. Additionally, a reproductive control agent is unlikely to avoid the bait due to ill health effects associated with sampling, as is often the case with a lethal pesticide.

In addition to the acid, gas-liberating neutralizing agent, surfactant foaming agent, and active ingredient, an inventive granule optionally contains a filler and/or binder. A filler operative herein is intended to provide a low-cost volume enhancement. Fillers operative herein illustratively include cereal or grain hulls, peanut hulls, plant pulp, other plant-based cellulose materials, and clays. A filler is typically present from 0.1 to 99.9 total weight percent and preferably from 5 to 98 total weight percent. A filler if present typically is dried to a water content of between 4 to 8 total weight percent.

Optionally, an inventive granule has a binder component present in an amount ranging from 5% to 75% by weight of the total dry weight of the granule. In a further embodiment, the binder component is present in an amount ranging from 1% to 25% by weight of the total dry weight of the granule. A binder component is included in a granule as necessary to produce or promote cohesion in forming a particle capable of retaining a specified form during transport and/or distribution. A binder component may be locust bean gum; vegetable oils such as corn, soybean, peanut, canola, olive, and cottonseed; or paraffin. Binders operative herein also include synthetic organic polymers capable of promoting or producing cohesion of particle components and such binders illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex.

An inventive granule is produced by a number of processes. In the preferred process, the granule components are wet granulated through a process of steps, including mixing of these components, wet massing the dry powder mixture with the biomaterial desiccant, the surfactant, and optional additives such as binders or the like, alone or with the addition of a solvent to arrive at a suitable consistency for granulating. It is appreciated that the solvent is limited in water content and the ability to initiate reaction between the acid and gas-emitting neutralizing agent. Optionally, an inventive composition is coated with a binder material, detackifier, varnish or latex to improve storage or flowability characteristics with a passivating surface coat.

Another preferred process is the homogenization by milling and/or blending of several powdered ingredients, including the stabilizing biomaterial desiccant mentioned above. The powder blend may be packaged as is, or granulated by means of dry (waterless and/or free of additional polar substances) compaction to form tablets, granules, or sticks which are then packaged or otherwise stored pending use.

An alternative embodiment from the inventive granule involves compressing a powder mixture into a large form that is subsequently ground to a desired size. It is appreciated that dry granulation is facilitated by the addition of a pressing agent, such as a stearate salt.

Alternatively, a granule omitting either an acid or neutralizing agent is impregnated with the omitted ingredient through solvent impregnation. The solvent means are selected to carry the omitted ingredient into the interior of the granule without complete activation of the acid neutralization reaction. As such, aqueous solvent is an unacceptable solvent, whereas anhydrous alcohols, ethers, tetrahydrofuran, and alkanes are generally suitable. It is appreciated that solvent impregnation is enhanced by allowing some gas formation, so as to open pores within the granule, thereby enhancing impregnation. Alternatively, wetting of a granule, a solvent carrying the omitted ingredient, followed by increasing the temperature, so as to volatize the solvent, is also operative herein.

In instances where the acid component exists as a hydrated powder, a fusion method is available in which to form an inventive granule. Heating of the mixed powder dissociates water from the acid, thereby causing some gas evolution, resulting in a pliable amorphous mass that is amenable to pass through a sizing screen. As heating temperatures typically are required in the range of 80-150° C., it is appreciated that the inclusion of the BAI subsequent to granule formation and drying is often preferred. Other ingredients such as the gas-evolving acid neutralizing agent are folded into the pliable acid mass. Subsequent addition of an active ingredient occurs through coating of the granule so formed with a binder solution containing the active ingredient. The resulting granule includes the desired amount of the active ingredient and has a sealant coat that impedes atmospheric degradation of the inventive granule.

In a de-icing or anti-icing use environment, inventive granules are dispersed onto a surface such as a road surface or piece of equipment to react, creating a foam that melts ice or prevents ice formation. It is appreciated that a resultant surfactant film inhibits ice nucleation.

It is appreciated that an inventive granule is operative alone, or as an additive with conventional pelletized substances, such as fertilizer, de-icer, or pest attractant bait.

The present invention is further detailed with respect to the non-limiting examples.

Comparative Core-Shell Segregated Composition Example 13.7 lbs (6.2 kg) of citric acid (with a 0.05% moisture content) is combined with slightly more than 3 mole equivalents of potassium bicarbonate (21.4 lbs (9.7 kg) as dry powders with a 0.05% moisture content) in a stainless steel vessel, together with 500 grams of sodium dodecyl sulfate and 22 lbs (10 kg) of −40 mesh corncob grind (3% moisture content). The resulting mixture is heated to 100° C. with constant turning. Upon softening to a paste consistency, the material is urged through a No. 6 sieve and cooled. The resulting granules are then coated with an anhydrous (<0.01% by weight water) isopropanol solution of methylene ureas containing 0.3% by weight methylparathyon and allowed to dry to a hard-dry coating. The resulting comparative granules have a storage stability in 70° C., 70% relative humidity testing chamber of 24 hours.

The resulting granules are broadcast onto a wet turf crop field. The granules are observed to adhere to leaf and plant surfaces with acid neutralization-based foaming observed immediately thereafter.

Comparative Homogeneous Composition Example

The components of the above comparative core-shell example are homogenously mixed and form granules as detailed above. The resulting granules have a storage stability of 20 minutes in the humidity testing chamber.

EXAMPLE 1

The composition of the comparative homogeneous example is formed with the exception that the anhydrous isopropanol contains 10 solution weight percent lignin to achieve a dried inventive granule having 25 total weight percent lignin. The component is pre-dried to 0.05 percent moisture prior to mixing. The resulting inventive granules have a storage stability in 70° C., 70% relative humidity testing chamber of 24 hours.

EXAMPLE 2A 13.7 lbs (6.2 kg) of citric acid (with a 0.05% moisture content) is combined with slightly more than 3 mole equivalents of potassium bicarbonate (40.6 lbs (18.4 kg) as dry powders with a 0.05% moisture content) in a stainless steel vessel, together with 2.9 lbs (1.3 kg) of 0.05 moisture content dry albumen. The resulting mixture is compressed into 0.5 kg disks which are ground to a −10 mesh size. The resulting inventive granules have a storage stability in 70° C., 70% relative humidity testing chamber of 24 hours. Moisture-barrier packaged stability of the inventive granules is in excess of 3 months.

EXAMPLE 2B

The procedure of Example 2A is repeated with the inclusion of 50 grams of glyphosate mixed homogenously therethrough. Upon dispersion onto wet soybean seedlings in a greenhouse, foaming is noted with greater than 95 number percent of the granules foaming while adhered to leaf or stem portions of the foliage.

EXAMPLE 3

13.3 lbs (6.1 kg) of citric acid is combined with slightly more than 3 mole equivalents of potassium bicarbonate (21.4 lbs (9.7 kg) as dry powders) in a stainless steel vessel, together with 0.3 lbs (136 grams) of the free acid form of bentazon, and 4.4 lbs (2 kg) of albumen. The resulting mixture is slurried with 22 liters of anhydrous methylene ureas to a paste consistency and compressed through a No. 4 pellet dye and evaporated to dryness with solvent reclaim. The resulting granules have a storage stability in 70° C., 70% relative humidity heating chamber of 24 hours. The granules formed a foam of bentazon-sodium salt upon water drenching.

EXAMPLE 4

The granules of Example 3 are made and overcoated with a 0.1 millimeter thick coating of ethyl acetate from an anhydrous solution in dichloromethane. The resulting inventive granules have a storage stability in 70° C., 70% relative humidity testing chamber of 24 hours.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process for inhibiting growth of a plant comprising:

forming a homogeneous storage stable gas-evolving pelletized composition comprising:

an herbicide present from 0.05 to 50 total weight percent;

an acid;

a gas-evolving acid neutralizing agent of at least one of an inorganic carbonate, inorganic bicarbonate, alkaline peroxide, or alkaline azide present from 1 to 60 total weight percent; and a water-soluble biomaterial desiccant homogeneously intermixed with said acid and said gas-evolving acid neutralizing agent;

said water-soluble desiccant present in an amount able to absorb an ambient moisture equivalent to at least 0.01 total weight percent of the composition as formed before gas evolution of more than 50% of the theoretical composition;

a surfactant foaming agent present from 0.1 to 10 total weight percent;

a foam stabilizing agent said acid, said gas-evolving neutralizing agent, said foaming agent; and said water-soluble desiccant cumulatively having less than 1 total weight percent water;

wetting the plant with water;

spreading said composition onto the plant;

allowing sufficient time for said composition to absorb the water and evolve gas to form a foam containing said herbicide thereby spreading said herbicide on the plant; and maintaining said foam over time through the action of said foam stabilizing agent.

2. The process of claim 1 wherein said herbicide is glyphosate.

3. The process of claim 1 wherein said composition is formed as a plurality of −10 mesh granules.

4. The process of claim 1, wherein said acid is citric acid.

5. The process of claim 1, wherein said neutralizing agent is a carbonate.

6. The process of claim 1, wherein the foam stabilizing agent is one of glycerin, hydrolyzed protein, a synthetic polymer or a long chain polar compound with a straight chain hydrocarbon group of about the same length as said surfactant foaming agent.

7. The process of claim 6, wherein said surfactant foaming agent is a nonionic surfactant.

8. The process of claim 6, wherein said desiccant is a protein.

9. The process of claim 6, wherein said desiccant is lignin, a lignin salt, or albumen.

10. The process of claim 6, wherein said herbicide is an acid that is converted to a salt upon composition drenching.

11. The process of claim 10, wherein said acid is at least one of glyphosate, glufosinate, clopyralid, bentazon, picloram, and triclopyr.

12. The process of claim 10, wherein said acid is at least one of gibberellic acid, glutamate(GABA), atrimmec, trinexepac-ethyl, I-naphthalenacetic acid, phthalmic acid, carboxypeptidase A(3-CPA), indolebutyric acid, 4-chlorphenoxyacetic acid, chitsan hydroxyphenyl acetamide(CHPA), deltrol, clofencoet, and l-lactic acid.

* * * * *